(12) United States Patent
Hill, Jr. et al.

(10) Patent No.: US 8,085,301 B2
(45) Date of Patent: Dec. 27, 2011

(54) COMPACT HANDHELD DETECTOR FOR GREENHOUSE GASSES

(75) Inventors: Ralph Henry Hill, Jr., San Antonio, TX (US); Joseph Nathan Mitchell, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 515 days.

(21) Appl. No.: 12/381,767

(22) Filed: Mar. 16, 2009

(65) Prior Publication Data

US 2010/0231722 A1 Sep. 16, 2010

(51) Int. Cl.
*H04N 5/33* (2006.01)
(52) U.S. Cl. .................. 348/164; 250/339.06
(58) Field of Classification Search .......... 348/164; 250/339; 356/437
See application file for complete search history.

(56) References Cited

U.S. PATENT DOCUMENTS

| | | |
|---|---|---|
| 3,585,436 A | 6/1971 | Beijer et al. |
| 3,763,392 A | 10/1973 | Hollister |
| 3,848,970 A | 11/1974 | Goodell |
| 4,555,627 A | 11/1985 | McRae, Jr. |
| 4,755,675 A | 7/1988 | Rosenfeld et al. |
| 5,412,681 A | 5/1995 | Eisel et al. |
| 5,523,569 A | 6/1996 | Hornfeld et al. |
| 6,768,127 B1 | 7/2004 | Eggers et al. |
| 2002/0071122 A1 | 6/2002 | Kulp et al. |
| 2007/0018104 A1 | 1/2007 | Parvin et al. |
| 2009/0127478 A1 | 5/2009 | Inoue et al. |

FOREIGN PATENT DOCUMENTS

WO 2007139022 A1 12/2007

OTHER PUBLICATIONS

EIS, "Home, Welcome to Equipment Imaging and Solutions, Inc.," available at http://www.sf6detection.com/; retrieved on Nov. 19, 2008.
Access Laser Company, "Low Power CO2 Laser," available at http://www.accesslaserco.com/PDF/Spec%20Lasy3.pdf; retrieved on Nov. 19, 2008.
McRae, "Gas Value and the Magnesium Industry: Advanced SF6 Leak Detection," EPA Conference on SF6 and the Environment: Emission Reduction Strategies, San Diego, CA, Nov. 2-3, 2000; available at www.epa.gov/electricpower-sf6/documents/conf00_mcrae.pdf(Power Point Presentation).
Access Laser Company, "Products," available at http://www.accesslaserco.com/Products.htm; retrieved on Nov. 19, 2008.
"Absorption of Infrared Radiation," available at http://www.habmigern2003.info/future_trends/infrared_analyser/ndir/IR-Absorption-GB.html; retrieved, Dec. 15, 2008 (author unknown).

(Continued)

*Primary Examiner* — Joseph Avellino
*Assistant Examiner* — Marshall McLeod
(74) *Attorney, Agent, or Firm* — Grossman, Tucker et al.

(57) ABSTRACT

Techniques are disclosed relating to gas leak detection. The techniques can be deployed, for example, in compact, handheld portable devices usable for detecting leaks in space-confined applications. The devices generally include an unstablized laser and thermal imaging camera that allow for detection of gas that absorbs at least some of the wavelength of operation of the unstablized laser. The devices can be operated at a low-power density for safety and/or may be configured to mitigate wavelength hopping associated with unstablized laser light sources.

9 Claims, 7 Drawing Sheets

OTHER PUBLICATIONS

McRae, "GasVue and the Magnesium Industry: Advanced SF6 Leak Detection," available at www.epa.gov/electricpower-sf6/documents/conf00_mcrae_paper.pdf; retrieved on retrieved Nov. 18, 2009.

Nowak, et al, "The Temperature-Dependent Absorption Spectrum of the V3 Band of SF6 At 10-6 um+", J.Quant. Spectrosc. Radiat. Transfer. vol. 15, No. 10-E, pp. 945-961, Pergamon Press 1975. Printed in Great Britian.

"Spectral Remote Sensing and Detection"; home page; available at http://www.spectralcorp.com/index.html; retrieved Apr. 20, 2009.

"Spectral Remote Sensing and Detection"; EO/IR Products page; available at http://www.spectralcorp.com/html/eo_ir_products.html; retrieved Apr. 20, 2009.

"Spectral Remote Sensing and Detection"; Gas Leak Detection page; available at http://www.spectralcorp.com/htm/gas_leak_detection.html; retrieved Apr. 20, 2009.

"Spectral Remote Sensing and Detection"; BAGI Systems page; available at http://www.spectralcorp.com/html/bagi_systems.html; retrieved Apr. 20, 2009.

"Spectral Remote Sensing and Detection"; GasVue page; available at http://www.spectralcorp.com/html/_gasvue.html; retrieved Apr. 20, 2009.

"Spectral Remote Sensing and Detection"; GasVue II page; available at http://www.spectralcorp.com/html/_gasvue_ii.html; retrieved Apr. 20, 2009.

"Spectral Remote Sensing and Detection"; Laser Line-Scan Camera (LLC) page; available at http://www.spectralcorp.com/html/llc_retrieved Apr. 20, 2009.

U.S. Non-Final Office Action issued Nov. 15, 2010 in U.S. Appl. No. 12/381,768 (13 pages).

U.S. Office Action issued Apr. 29, 2011 in related U.S. Appl. No. 12/381,768.

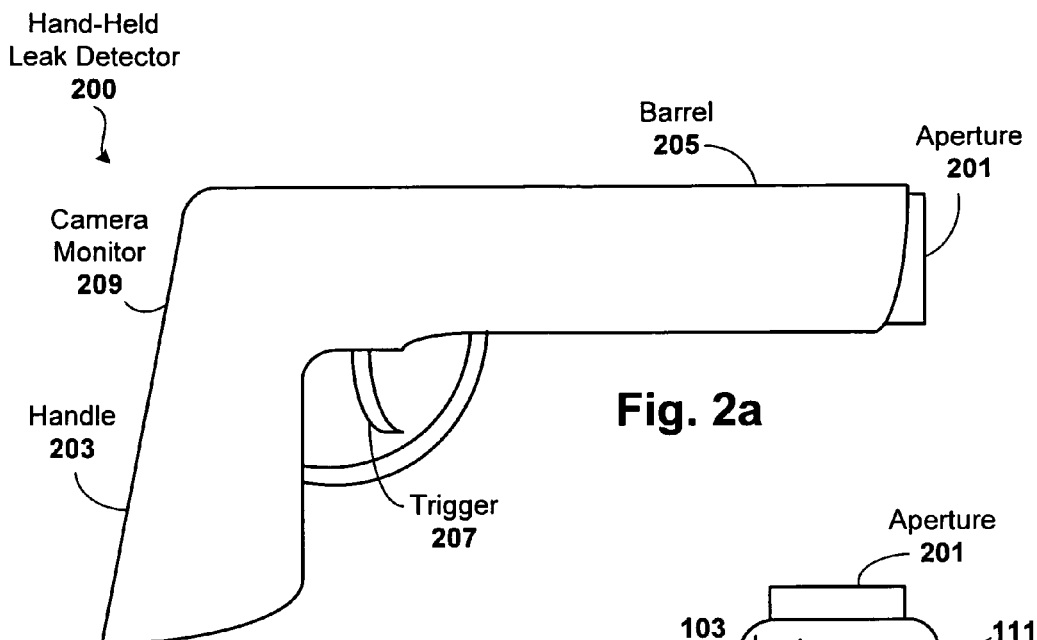
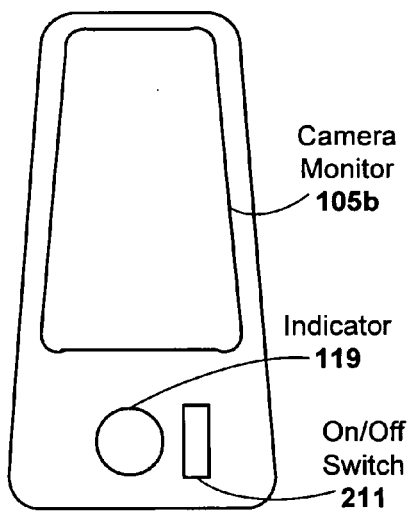
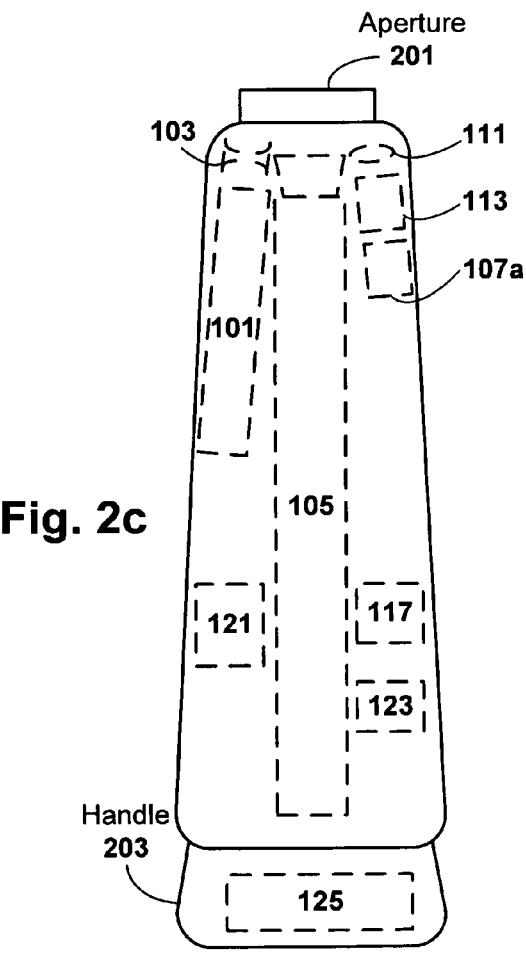

US 8,085,301 B2

COMPACT HANDHELD DETECTOR FOR GREENHOUSE GASSES

STATEMENT OF GOVERNMENT INTEREST

The invention was made with United States Government support under contract DAAB07-03-D-B009 awarded by the U.S. Air Force, and the United States Government may have certain rights in this invention.

RELATED APPLICATION

This application is related to U.S. application Ser. No. 12/381,768, filed Mar. 16, 2009, and titled "Compact Handheld Non-Laser Detector for Greenhouse Gasses" which is herein incorporated by reference in its entirety.

FIELD OF THE INVENTION

The invention relates to gas leak detection, and more particularly, to techniques that can be employed in compact, handheld devices for detecting leaks in relatively small spaces.

BACKGROUND OF THE INVENTION

There is presently a great need to locate leaks of so-called "greenhouse" gases such as sulfur hexafluoride ($SF_6$). As is generally known, higher concentrations of greenhouse gases in the atmosphere cause infrared (IR) radiation released from the earth to become trapped in the lower atmosphere. As a result of this trapped radiation, the lower atmosphere tends to warm, which in turn impacts the Earth's weather and climate. Other common greenhouse gasses generally caused by human activity include carbon dioxide ($CO_2$), methane ($CH_4$), chlorofluorocarbon (CFC), hydrofluorocarbon (HFC), and ozone ($O_3$).

In general, absorption techniques can be used to detect many such gases. However, there are a number of limitations associated with such conventional techniques. For instance, absorption techniques in the thermal IR range are not effective if the background temperature is similar to the temperature of the target gas to be detected, because there is almost no contrast between the background and the target gas. In addition, image contrast can be weak, caused by other factors, such as inhomogeneous illumination and weak absorption. Because of these problems, techniques to enhance the contrast have been proposed.

These conventional techniques generally increase the image contrast utilizing a laser illuminator. One such technique is provided in U.S. Pat. No. 4,555,627, titled "Backscatter Absorption Gas Imaging System," which describes absorption techniques to image hazardous gases. In particular, the disclosed technique uses a flying spot IR laser beam and video imaging system, and detects hazardous gases which are highly absorbed by the laser beam. Cameras based on similar techniques have been developed to detect $SF_6$ (e.g. GasVue and GasVue II camera product lines). However, these cameras are large and bulky (typically shoulder mounted units that are coupled to power and cooling units via heavy cabling), and therefore are application limited. For instance, such techniques cannot be implemented inside confined spaces or otherwise close quarters, such as within the fuselage of an airplane or other vehicle that may be equipped with gas-containing gear (e.g., radar equipment).

There is a need, therefore, for gas leak detection techniques that can be deployed, for example, in compact, handheld devices usable for detecting leaks in space-confined applications.

SUMMARY OF THE INVENTION

One embodiment of the present invention provides a gas leak imaging system. The system includes an unstabilized laser for providing a laser beam having at least one wavelength that is absorbable by a target gas, a thermal imaging camera having a field of view and for imaging absorption of the at least one wavelength by the target gas, and a diverging lens for expanding the laser beam toward the field of view. The system is contained in a handheld housing (e.g., handgun or telescope shaped housing). The target gas can be, for example, sulfur hexafluoride ($SF_6$), or any other gas detectable using the techniques described herein. The unstabilized laser can be, for example, a $CO_2$ infrared laser. The camera can be, for example, a longwave infrared camera. Other targets gasses, unstabilized lasers, and cameras will be apparent in light of this disclosure. The system may include circuitry for mitigating wavelength hopping associated with the unstabilized laser. In one such embodiment, the circuitry for mitigating wavelength hopping includes a detector for receiving light from the unstabilized laser and generating an electrical signal representative of intensity associated with that light, and a circuit for receiving the electrical signal and, based on that signal, indicating when the at least one wavelength that is on-resonance with absorption lines of the target gas. In one such case, the circuit for indicating when the at least one wavelength that is on-resonance with absorption lines of the target gas includes a comparator for receiving the electrical signal and comparing that signal to a known threshold that is representative of a minimum required light intensity signal, and an indicator for indicating, based on output of the comparator, when the at least one wavelength is on-resonance with absorption lines of the target gas. In another such case, the light received by the detector can be, for example, one of reflected back from the field of view, or split off from the laser beam provided by the unstabilized laser (or a combination of the two). The system may include circuitry for reducing power density associated with the unstabilized laser (e.g., for safety purposes and/or power conservation). In one such embodiment, the circuitry for reducing power density includes one of more of the following: an oscillator for modulating the unstabilized laser, a vertical blanking interval detector for receiving a video output of the thermal imaging camera and detecting when the vertical blanking interval is occurring (thereby allowing the unstabilized laser to be turned off during that interval), a horizontal blanking interval detector for receiving a video output of the thermal imaging camera and detecting when the horizontal blanking interval is occurring (thereby allowing the unstabilized laser to be turned off during that interval), and/or an image detector for receiving a video output of the thermal imaging camera and detecting when a scan line of the camera is active, thereby allowing the unstabilized laser to be turned off when no image data is present.

Another embodiment of the present invention includes a gas leak imaging method. The method includes providing a laser beam from an unstabilized laser to a field of view, the laser beam having at least one wavelength that is absorbable by a target gas. The method further includes expanding the laser beam toward the field of view, and imaging absorption of the at least one wavelength by the target gas. The unstabilized laser is contained in a handheld device that is capable of carrying out the method. The method may further include mitigating wavelength hopping associated with the unstabilized laser, and/or reducing power density associated with the unstabilized laser.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

FIG. 2a is perspective view of a handheld gas leak detector, configured in accordance with another embodiment of the present invention.

FIG. 2b is end-view of the handheld gas leak detector shown in FIG. 2a.

FIG. 2c is top-view of the handheld gas leak detector shown in FIG. 2a, with internal components shown in dashed lines.

FIG. 3b is end-view of the handheld gas leak detector shown in FIG. 3a.

DETAILED DESCRIPTION OF THE INVENTION

Figure 1A:
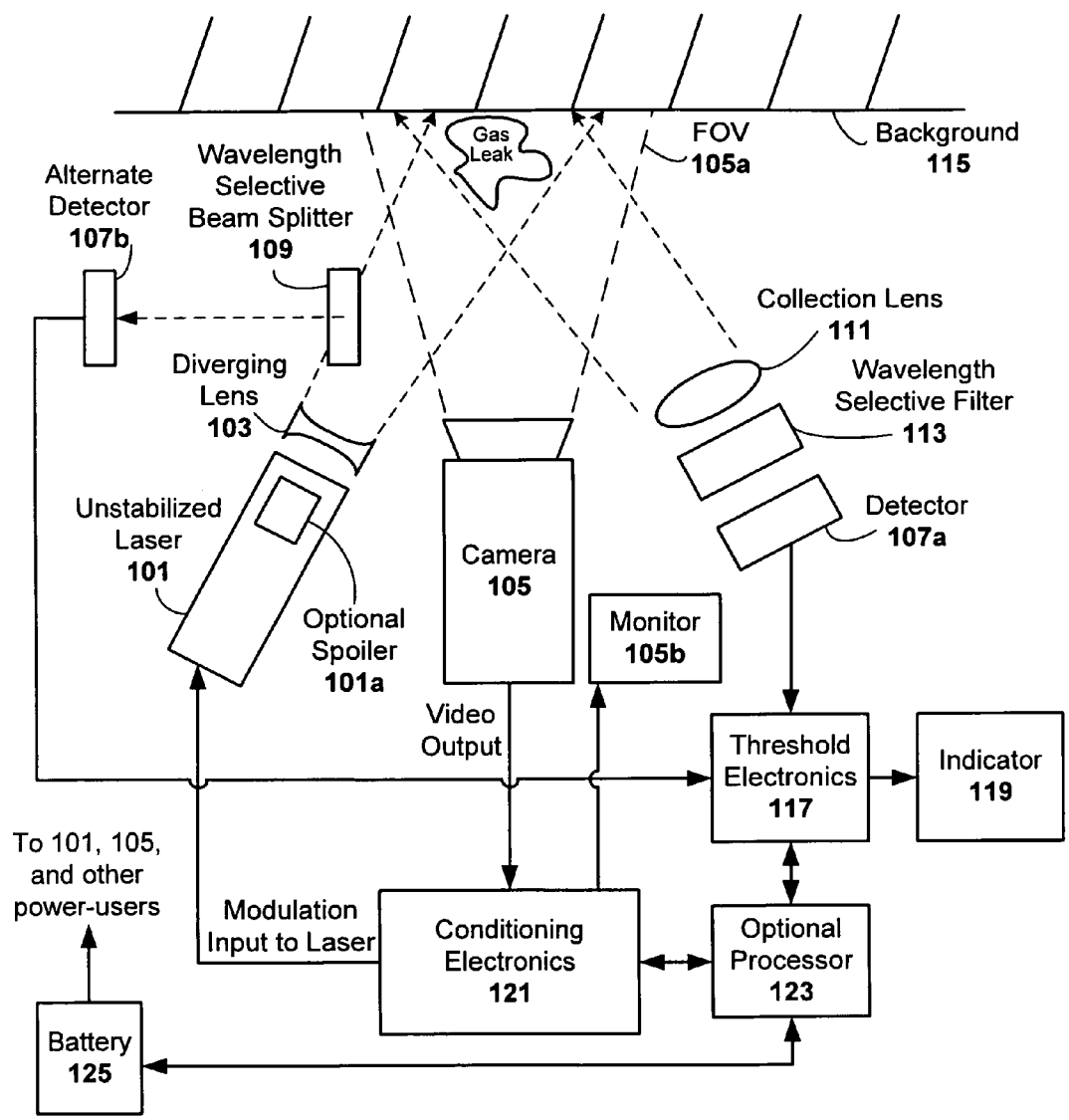
FIG. 1a is a laser-camera gas leak detection system, configured in accordance with an embodiment of the present invention.

Techniques are disclosed relating to gas leak detection. The techniques can be deployed, for example, in compact, handheld portable devices usable for detecting leaks in space-confined applications. The devices generally include an unstablized laser and thermal imaging camera that allow for detection of gas that absorbs at least some of their wavelengths of operation. The devices can be operated at a low-power density for safety and/or may be configured to mitigate wavelength hopping associated with unstablized laser sources. The techniques are suitable for use, for instance, in detecting gas leaks within the fuselage of an airplane or other vehicle that may be equipped with gas-containing gear (e.g., radar equipment), which may be leaking. Other such confined-space applications will be apparent in light of this disclosure.

General Overview

Imaging the infrared absorption of gasses such as $SF_6$ is generally known. However, as previously explained, such conventional detection techniques generally employ large units that are not suitable for space-confined applications. This longstanding design paradigm has generally not been challenged, as it is widely believed that gas leaks can be readily detected from a distance thereby allowing a nearby suitable and open space to be selected for the imaging and detection process to be carried out. Moreover, efforts to use smaller components (such as compact lasers) introduce a number of non-trivial problems.

For instance, conventional designs employ stabilized lasers which require cooling (e.g., water cooled lasers and air cooled lasers). Conventional cooling componentry tends to be bulky and heavy (e.g., cooling fans and/or water), and ultimately limits the form factor of the overall system to a relatively large size. An unstabilized (uncooled) laser will eliminate the need for such bulky/heavy cooling componentry associated with stabilized lasers, but is susceptible to wavelength hopping of the laser. In particular, an unstabilized laser may hop to a wavelength that is not absorbed by the target gas (e.g., $SF_6$, or other such greenhouse gas). The reason that the wavelengths hop around is because of thermal instabilities (given the lack of cooling). Another problem generally associated with using lasers in close quarters has to due with safety, and more specifically with the power density of the laser. Depending on the type of gas to be detected, the frequency of the laser may be in a range that is potentially harmful when the power density of that laser is sufficiently high.

Thus, and in accordance with one example embodiment of the present invention, a gas leak imaging system is provided that employs a relatively small unstabilized laser and wavelength hopping mitigation and/or power density reduction techniques. A diverging lens can be provided on the output of the laser to expand the beam, and a thermal camera can be used to image the infrared (IR) absorption of the target gas or gasses. The system is compact and can be implemented in a handheld unit (e.g., having a form factor similar to that of a hand-gun or telescope or other such form factors suitable for handheld operations) that can be brought into small spaces and aimed at target areas to carryout inspection and leak detection. In some such embodiments, the unstabilized laser and wavelength hopping mitigation techniques can be implemented within the infrared camera. In a more general sense, the functional components making up the system can be integrated into a compact housing suitable for handheld applications or otherwise in close quarters.

With respect to wavelength hopping mitigation, one example such technique involves detecting when the unstabilized laser beam is on-resonance or off-resonance. When on-resonance band wavelengths are detected, the corresponding images from the camera can be designated or otherwise used for detection purposes; otherwise, the images associated with off-resonance band wavelengths of the unstabilized laser can be discarded or otherwise ignored. Thus, in such a case, the system user will only be alerted to leaks when the laser beam is on-resonance (e.g., coincident with an $SF_6$ absorption, or other target gas or spectrum).

Another example wavelength hopping mitigation technique involves the use of a spoiler in the laser cavity to stop the lasing action on laser lines that are not on-resonance. The spoiler may take a number of forms, so long as it stops or otherwise quenches the off-resonance laser wavelengths. For instance, the spoiler can be an intracavity, wavelength selective mirror (e.g., that only passes on-resonance wavelengths to output aperture of laser) or absorber (e.g., that prevents off-resonance wavelengths from passing to output aperture of laser).

With respect to power density reduction, one example such technique involves turning the laser off during periods when the video signal has no image information on it due to timing and video housekeeping operations, such as during the horizontal blanking interval. Turning the laser off during such periods not only allows for a substantial laser-off period, but also lowers the average power density of the laser, while simultaneously providing the same detection sensitivity. Another example power density reduction involves turning the laser off during periods when the video signal has no image information on it due to being out of the field of view of the leak (i.e., when the laser itself is imaged because it is reflected back to the camera without any interaction with the target gas). Each of these power density reduction techniques can also be used to provide both a safety feature (lower power density), as well as a power management feature (battery conservation).

System Architecture

FIG. 1a is a laser-camera gas leak detection system, configured in accordance with an embodiment of the present invention.

As can be seen, the system includes a thermal imaging camera 105 having a field of view (FOV) 105a and monitor 105b, and an unstabilized laser 101 optically coupled with a diverging lens 103. In addition, the system includes a detector 107a optically coupled to a filter 113 and an optional collection lens 111. Alternatively, or in addition to, the system may include a detector 107b and beam splitter 109. In short, these alternate/supplemental detection schemes (i.e., detector 107a and filter 113 and lens 111, or detector 107b and beam splitter 109) allow for wavelength hopping mitigation, as will be explained in turn. Threshold electronics 117 is operatively coupled to detector 107a and/or 107b, and also to indicator 119 and an optional processor 123. In addition, camera 105 is operatively coupled to conditioning electronics 121, which is also operatively coupled to processor 123. The system also includes a battery 125, which is connected (connections not shown to avoid cluttering the figure) to any components requiring power (e.g., electronics 117 and 121, camera 105, laser 101, detectors 107a-b, processor 123, and indicator 119). Battery 125 may also be operatively coupled to processor 123 for control purposes (e.g., power management scheme).

In operation, the gas leak imaging system can be used to detect gas leaks by directing a beam from laser 101 into the FOV 105a of camera 105 and toward the background area 115 (which can be any area where leaks of the target gas might be). The laser beam is expanded by the diverging lens 103 to provide wider coverage by the beam. When the laser beam is projected into the FOV 105a, the infrared absorption of the leaking gas is imaged (e.g., FIG. 4) by the infrared camera 105 on monitor 105b (a conventional monitor which may be internal to camera 105 or external and operatively coupled thereto). The laser 101 can be, for example, a radio-frequency (RF) excited nominal 10.6-micron $CO_2$ laser and the camera 105 can be, for example, a longwave infrared camera, thereby allowing the system to image the infrared absorption of $SF_6$ or other gas that absorbs radiation within that range. In one such specific embodiment, the laser 101 is implemented with a Lasy-3 series laser (from Access Laser Company), and the longwave IR camera 105 is implemented with a FLIR model 65HS (from FLIR Systems, Inc), or a Fluke model Ti55 (from Fluke Corporation). The diverging lens 103 can be implemented with conventional optics configured for the wavelength range of interest (e.g., 10.5 and 10.7 microns), and in one example case is an 18-mm focal length zinc selenide (ZnSe) diverging lens. Thus, the system can be implemented with an off-the-shelf small unstabilized $CO_2$ laser, diverging lens, and an infrared camera. Other such suitable compact unstabilized lasers and thermal imaging cameras can be used as well, depending on factors such as target gas to be detected. The battery 125 can be implemented with conventional technology (e.g., rechargeable NiMH or Li-ion batteries), and is capable of providing sufficient power to the system. In some embodiments, battery 125 may be distributed, wherein individual components making up the system each have their own battery. Conventional power conditioning techniques may also be employed, if so desired (e.g., regulation, filtering, etc). An AC adapter may also be provided for charging the battery 125 (or batteries). Numerous suitable variations and alternative power schemes can be used here.

Thus, a compact portable gas leak imaging system is provided. Any number of gas leaks can be detected depending on the system configuration. In one specific example embodiment, $SF_6$ leaks can be detected on the order of 1 sccm (standard cubic centimeter per minute) or less using a Lasy-3 laser (for laser 101), an 18-mm focal length zinc selenide diverging lens (for lens 103) to expand the beam, and a FLIR model 65 HS longwave infrared camera (for camera 105). The entire system weighs about 10 lbs or less and can easily be handheld. Example form factors for the housing containing the system include a hand-gun or telescope shaped housing, although any number of suitable form factors can be used. Thus, handheld as used herein means that the system (or device, apparatus, etc) is small and light enough to be operated while an appropriate user holds it in one or both hands. An appropriate user may be, for instance, a man or woman capable of holding about 10 lbs in one or both hands (e.g., while arms are extended in front of the user or while the user's elbows are supported on a table or other suitable surface). Note that the system may optionally include, for example, a lanyard (cord worn around the neck and operatively coupled to the system) so that the system can hang from the lanyard during periods of non-use, and even while being used or otherwise manipulated by the user's hand or hands. A small tripod may also be used to support such a compact system, if so desired. The system can be operated, for example, to view targets in close proximity (e.g., less than a meter away), although viewing target areas at greater distances away (e.g., three meters or more) is possible as well using the appropriate optics, if needed and as will be apparent in light of this disclosure. In one specific such embodiment, the target wavelength operation is near 10.551 microns.

The system shown in FIG. 1a also includes a number of optional components associated with wavelength hopping mitigation and power density reduction. In particular, the system of this example embodiment demonstrates three wavelength hopping mitigation techniques (hereinafter mitigation techniques #1, #2, and #3, respectively), and three power density reduction techniques (hereinafter power density reduction techniques #1, #2, and #3, respectively).

Optional processor 123 can be used to enable or otherwise select certain modes of operation (e.g., by enabling one or more mitigation and/or power density reduction techniques), and/or implement other functionality such as power conservation schemes and report generation. The processor 123 may be implemented, for example, with a conventional processing environment such as a programmable gate array (e.g., ASIC or FPGA) or a microcontroller having a number of input/output ports and executable routines for carrying out desired functionality. The processor 123 may operate in conjunction with a user interface that allows the user to configure a desired mode of operation. This interface can be, for example, hardware-based (e.g., toggle switches that can be set to enable/disable modes of operation) or software-based (e.g., graphical user interface that can be manipulated to enable/disable modes of operation). In one particular embodiment, the processor 123 responds to user input to activate the detection system (e.g., by enabling the laser 101 and/or camera 105). In addition, should the detection system remain dormant (unused) for a period of time, the processor 123 may be configured to implement a power conservation scheme, where laser 101 and camera 105 are disabled to a low-power (or no-power) consumption mode. Such conservation schemes will help preserve the life of battery 125. Numerous configurations and functions for processor 123 will be apparent in light of this disclosure.

Wavelength Hopping Mitigation

As previously explained, unstabilized laser sources are susceptible to wavelength hopping (e.g., about 50% of the time). The reason for this is that unstabilized lasers operate between several wavelengths (sometimes designated as the 10R branch and the 10P branch in $CO_2$), due to thermal instabilities. For instance, an unstabilized RF excited nominal 10.6-micron $CO_2$ laser (e.g., such as the Lasy-3) operates at wavelengths between approximately 10.195-10.289 microns (10R branch) and 10.494-10.696 microns (10P branch). However, and assuming that $SF_6$ is the target gas (for example), note that $SF_6$ absorption lines are between approximately 10.513 and 10.719 microns. Thus, when the laser is operating in the 10R range and in some portions of the 10P range, no $SF_6$ absorption will occur and accurate detection cannot take place because the laser beam is off-resonance. Said differently, accurate detection of the target gas takes place when the laser beam is on-resonance, meaning that the laser beam wavelength is coincident with the target gas absorption lines.

Figure 1B:
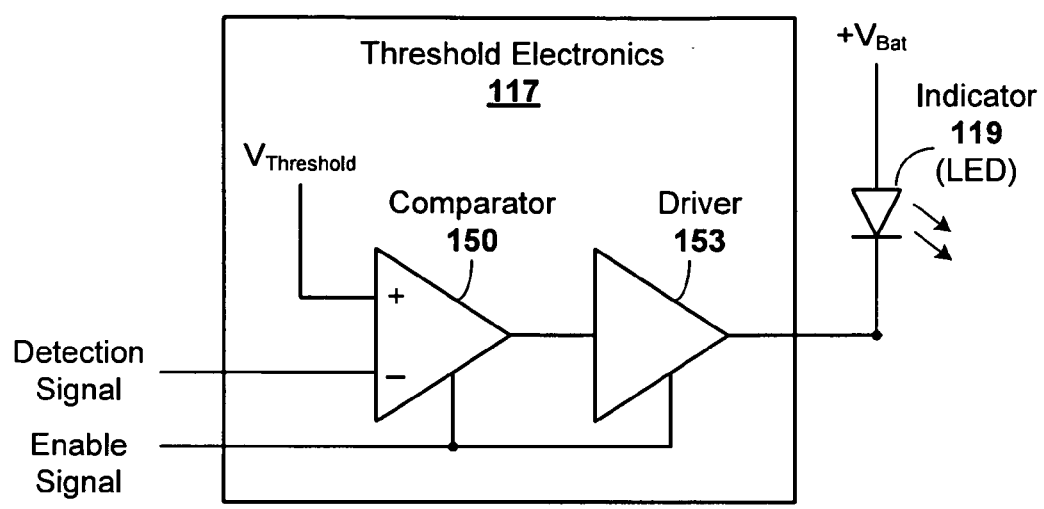
FIG. 1b is an example threshold electronics circuit of the system shown in FIG. 1a, configured in accordance with an embodiment of the present invention.

Mitigation technique #1 involves detecting when the laser beam is on-resonance or off-resonance. In more detail, this technique employs collection lens 111, filter 113, detector 107a, threshold electronics 117, and an indicator 119. As the laser beam from laser 101 reflects off of the background 115, some of the light from the reflected beam reaches collection lens 111, which focuses the collected light into the filter 113. The filter 113 removes unwanted light from the detection path to the detector 107a, which detects light passed by the filter 113 and generates an electrical signal representative of the light intensity detected. In one specific example case, filter 113 is configured for $SF_6$ detection and is implemented as a narrow-band interference filter configured to have a central wavelength of about 10.5638 microns and a bandwidth 0.4329 at the 10% transmission points (available from Spectrogon). The detector 107a can be implemented, for example, with a photodiode or focal plane array or charge-coupled device array, depending on factors such as desired cost and complexity. Threshold electronics 117 receives the detection signal from detector 107a, and outputs a control signal that indicates when the laser beam is on-resonance or off-resonance. In the example embodiment shown in FIG. 1b, the electronics 117 includes comparator 150 comparing the detection signal to a known threshold ($V_{Threshold}$) that is representative of a minimum required light intensity signal from detector 107a. If necessary, a driver 153 can be used to amplify or otherwise drive the comparator output signal to the indicator 119. If the detection signal from detector 107a is equal to or greater than $V_{Threshold}$, then the electronics 117 outputs a low signal, which causes current to flow through the indicator 119 (which in this example embodiment is an LED), thereby indicating the laser beam is on-resonance. On the other hand, if the detection signal from detector 107a is less than $V_{Threshold}$, then the electronics 117 outputs a high, which effectively prevents current from flowing through the indicator 119, thereby indicating the laser beam is off-resonance. The $V_{Threshold}$ can be implemented, for example, with a voltage reference equivalent to 30% of the full intensity output signal of detector 107a. Thus, any detection signal greater than or equal to 30% of the full intensity output signal of detector 107a will cause a low signal output from comparator 151 and driver 153 to turn on indicator 119. The indicator 119 can be implemented, for example, with an LED (e.g., green LED for on-resonance), and/or an audible sound that can be heard (e.g., buzz or beep when on-resonance), and/or a vibration that can be felt such as cell-phone vibration technology (e.g., vibrate when on-resonance). In alternative embodiments, the threshold electronics 117 can be configured to disable, turn-off, or blank the monitor 105b when off-resonance (e.g., by way of a blank monitor input, or similar mechanism). Still in other embodiments, note that the threshold electronics 117 can be eliminated, particularly when the passband of filter 113 is well-defined (to the on-resonance band) and detector 107a outputs a detection signal having sufficient energy to drive the indicator 119. Other variations and adaptations will be apparent in light of this disclosure, and any number of suitable detection schemes can be used here. In any such cases, when on-resonance band wavelengths are detected, the corresponding images from the camera 105 can be designated or otherwise used for detection purposes; otherwise, the images associated with off-resonance band wavelengths can be discarded or otherwise ignored. Mitigation technique #1 therefore allows for visual and/or audible and/or vibratory cues, or other suitable indicators that distinguish when the laser is on-resonance (e.g., coincident with an $SF_6$ absorption) or off-resonance.

Mitigation technique #2 also involves detecting when the laser beam is on-resonance or off-resonance. However, in contrast to technique #1, technique #2 involves splitting off a small portion from the laser beam output using a wavelength selective beam splitter 109 and sending that small portion to detector 107b (as opposed to receiving laser light reflected back from the FOV 105a). The wavelength selective beam splitter 109 can be implemented with conventional optics, and may have a similar passband to that of filter 113. Detector 107b can be similar to detector 107a, and that previous discussion is equally applicable here, as is the discussion relevant to threshold electronics 117 and indicator 119. Note that in other embodiments, wavelength selective beam splitter 109 can be implemented with a separate conventional beam splitter and a wavelength selective filter (like dichroic filter 113). In any such cases, when on-resonance band wavelengths are detected, the corresponding images from the camera 105 can be designated or otherwise used for detection purposes; otherwise, the images associated with off-resonance band wavelengths can be discarded or otherwise ignored. Thus, just as with mitigation technique #1, leaks are effectively reported only when the laser beam is on-resonance (e.g., coincident with an $SF_6$ absorption).

Mitigation technique #3 involves the use of a spoiler 101a in the laser cavity of laser 101 to stop the lasing action on the laser lines that are not on-resonance. For instance, assume that laser 101 is implemented with a Lasy-3 laser and the target gas is $SF_6$. If the so-called 10R branch lines (e.g., 10.195-10.289 micron lines for a Lasy-3 laser) are quenched by the spoiler 101a, then the laser would effectively be operating only in the so-called 10P branch, most of which would be absorbed by the $SF_6$. Note that similar schemes having other lasers coincident with different target gasses will be apparent in light of this disclosure. The spoiler 101a may take a number of forms, so long as it quenches the off-resonance laser wavelengths. For instance, the spoiler 101a can be an intracavity, wavelength selective mirror or absorber. An existing laser design can be retrofitted with spoiler 101a, for example, by modifying the reflectivity of one of the output mirrors within the laser cavity. In one specific such example case, this mitigation technique can be implemented using a modified laser-cavity mirror which quenches the "10R" lines in a Lasy-3 $CO_2$ laser to view leaking $SF_6$ gas at leak rates on the order of 25 sccm or less from a pin hole. In this example case, the leak is imaged approximately 100% of the time, in that the $CO_2$ lines are on-resonance with the $SF_6$ absorption lines.

Power Density Reduction

As previously explained, safety considerations may make a relatively low power density of the laser desirable. For instance, a number of green house gasses are coincident with IR radiation having a wavelength that is potentially harmful (e.g., may cause tissue damage). However, by managing the power density, such laser wavelengths can be more safely used, particularly when the power density is reduced to a level where tissue damage does not occur. Maintaining a low power density may also be desirable from a power/battery conservation perspective.

Power density reduction techniques #1 through #3 each involves the use of conditioning electronics 121 along with the video output signal of camera 105 and the modulation input of laser 101. Assume, for example, that the laser beam from laser 101 is pulse-width modulated or gated on-and-off with at approximately 15 KHz, and that the video output of camera 105 is based on standard NTSC RS-170 video format. Because of the various timing signals associated with such as standard video format, the laser 101 does not always need to be on (i.e., when video signal has no image information on it due to timing and video housekeeping operations).

For instance, the entire period of an NTSC horizontal line is about 63.5 microseconds. The visible picture portion of this line takes approximately 52.7 microseconds. The remaining time, 10.8 microseconds, is the horizontal blanking interval (which includes the front porch, horizontal sync, color burst, and back porch), which has no visible picture associated with it. Thus, during the 10.8 μs horizontal blanking interval, the laser 101 can be turned off. This means that the laser would be turned off for about 17.0% of the time (per horizontal scan line). This is generally referred to herein as power density reduction technique #1.

Additionally, not all the scan lines include image information. For instance, the vertical sync pulse and equalizing pulses take up lines out of each field (as is known, there are two fields per frame). In short, out of 525 scan lines, only 480 of them (91.4%) are actually encoded with video information. Therefore, the laser 101 can be turned off during these periods as well. This is generally referred to herein as power density reduction technique #2.

Figure 4:
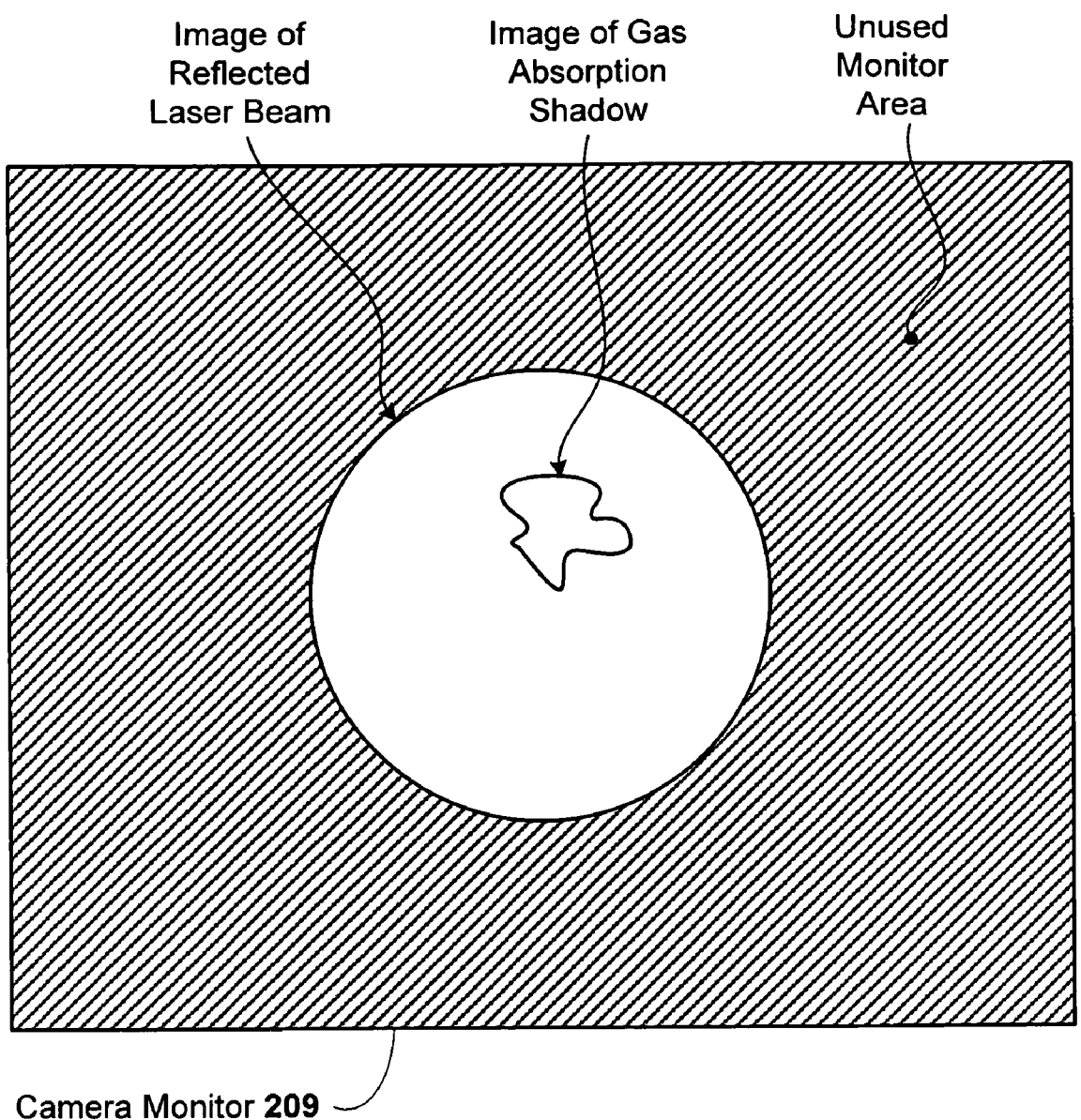
FIG. 4 illustrates an image of the infrared absorption of a gas detected by the system shown in FIG. 1a, in accordance with an embodiment of the present invention.

Additionally, in the example embodiments shown in FIGS. 1a and 4, a circular laser beam (from laser 101) is displayed on a rectangular image (monitor 105b). This means, at least in some instances, that there is wasted time when the laser beam could be turned off (i.e., when the video signal has no image information on it due to the FOV 105a not having a leak therein). This is generally referred to herein as power density reduction technique #3.

Figure 1C:
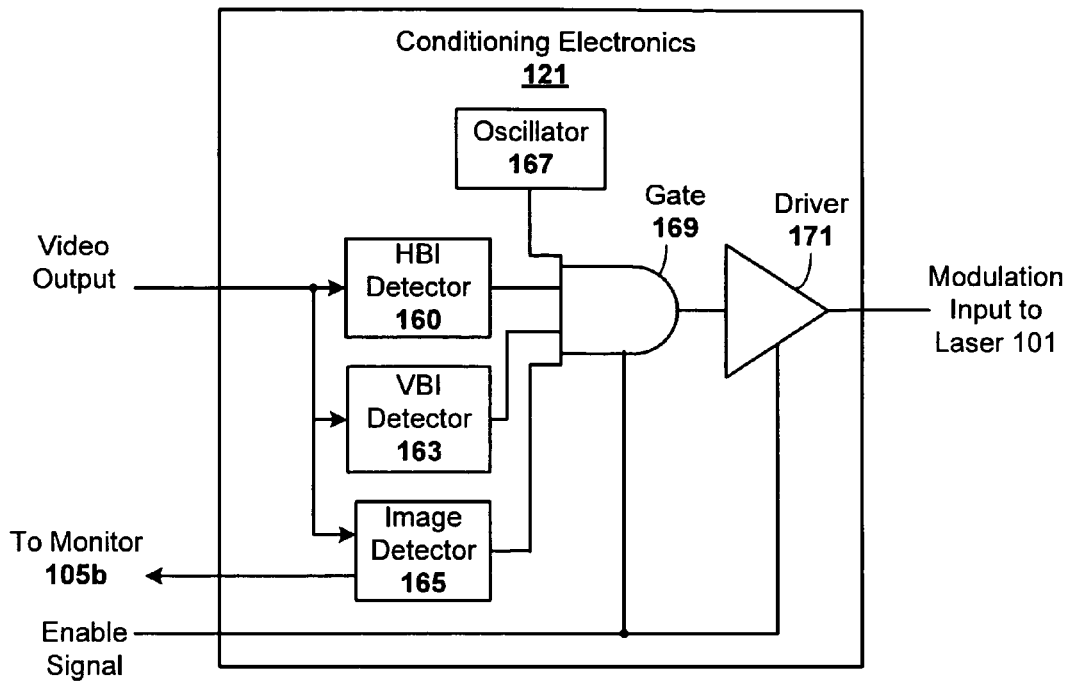
FIG. 1c is an example conditioning electronics circuit of the system shown in FIG. 1a, configured in accordance with an embodiment of the present invention.

Thus, by turning off the laser 101 when the video signal provided by camera 105 has no image information on it due to timing and video housekeeping operations, a substantial laser-off period can be accomplished. This means that the average power density of the laser 101 can be lowered to get the same detection sensitivity. In the example embodiment shown in FIG. 1c, the conditioning electronics 121 is implemented with circuitry configured to carryout each of power density reduction techniques #1, #2, and #3. In particular, conditioning electronics 121 is configured to receive the video signal output of camera 105, and to detect the occurrence of the vertical blanking interval (VBI) and horizontal blanking interval (HBI), as well as to detect when no gas leak is being imaged.

In more detail, electronics 121 includes an HBI detector 160 and a VBI detector 163, which can be implemented with conventional technology (e.g., positive and negative edge detection circuitry for detecting the beginning and end of the corresponding blanking intervals). In addition, the image detector 165 is configured to detect when a scan line of the camera is active. Additional details of image detector 165 are provided with reference to FIGS. 1d and 1e. Each of the outputs of the HBI detector 160, VBI detector 163, and the image detector 165 is provided to the input an AND gate 169. The output of oscillator 167, which provides the modulating frequency for the laser, is also provided to the input of AND gate 169.

Figure 1D:
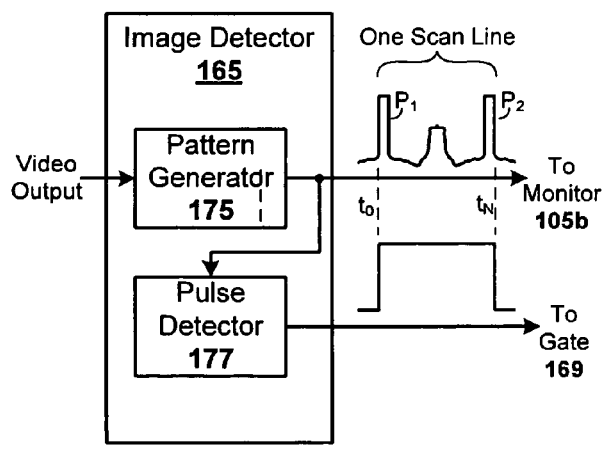
FIG. 1d illustrates an image detector configured in accordance with an embodiment of the present invention.

The image detector 165 can be implemented in a number of ways. FIG. 1d illustrates one example embodiment, which includes a pattern generator 175 and a pulse detector 177. In one such example case, assume that camera 105 is implemented with a FLIR model 65HS, which has a video output signal (on an RCA connector) that can be used to drive an external video monitor. Other thermal imaging cameras provide a similar output. This video output signal is provided to pattern generator 175, so that a desired pattern (voltage signal as a function of time) can be added to the video signal (voltage signal as a function of time). The desired pattern can be, for instance, a circle of variable diameter that can be positioned and otherwise adjusted (e.g., by manually turning an adjustment knob on the front panel or pattern generator 175, or using software) over the image of the laser beam (while looking at the monitor 105b). Assuming a circle is the desired pattern provided by generator 175, then on each video scan line by camera 105 there would be two large pulses $P_1$ and $P_2$ (as best shown in FIG. 1d), since the circle pattern would be white, and thus driven to the upper allowable limit (e.g., color white in accordance with the NTSC standard). This would happen on the left tangent of the circle and then again on the right tangent of the circle, thereby corresponding to the beginning and end of each scan line of the camera 105. Note that under the NTSC RS-170 standard, white is a signal with a voltage of greater than 714 millivolts above zero or 100 IRE units, where an IRE unit is the standard Institute of Radio Engineers unit for describing video signals. As can be further seen with reference to FIG. 1d, the output of generator 175 is sent to video monitor 105b (for viewing and calibration/adjustment of pattern) and also to the pulse detector 177. Either or both outputs provided by the generator 175 can be amplified if desired, to make sure the respective signal is sufficient to source the following electronics. In some cases, a video breakout amplifier can be used to split the generator 175 output into the two signals. The pulse detector 177 includes logic that detects the first pulse $P_1$ and second pulse $P_2$ associated with the circle pattern output by generator 175, and outputs a high signal during the time ($t_0$ to $t_N$) in between these two pulses, thereby indicating when image data such as a gas leak shadow is present in the video output. The pattern generator 175 can be implemented with conventional technology. A number of commercially available pattern generators allow for user defined custom patterns that can be submitted in various file formats such GIF, TIFF, or BMP (e.g., pattern generators by Microimage Video Systems, such as models PG311, or PG314, or PG 315, or the like). The pulse detector 177 can also be implemented with conventional pulse detection circuitry. In one specific embodiment, the pulse detector 177 is implemented with a comparator having a reference threshold that is just below upper allowable limit for white of the given standard (e.g., under the NTSC RS-170 standard, white is a signal with a voltage of greater than 714 millivolts above zero or 100 IRE units). Once that threshold is met, the comparator outputs a signal indicating the input signal has met or exceeded the threshold. This output signal can in turn can be used to trigger logic (e.g., such as a one shot timer or other suitable circuitry) to provide a logic high signal that lasts the duration of one scan cycle. One such example signal is shown in FIG. 1d, where the logic high output of pulse detector 177 is applied to gate 169.

In an alternative embodiment, the output signal of the pattern generator 175 can be added to the video out signal from the camera 105 using an adding circuit (such as an operational amplifier configured as an adder). The resulting signal can then be scaled so that it still conforms to the appropriate video signal standard (such as NTSC RS-170) voltage range. Further note that if the output of the adder circuit were not scaled in some way, the signal may be larger than it should be where the addition takes place; however, the generated pattern can be slightly saturated (so that the scaling circuitry may not be necessary). In cases having no scaling circuitry, consideration should thus be given to whether the unscaled signal will overload the following circuitry. A trigger circuit may be desirable in some embodiments, due to different delay times in the various components. For instance, all circuitry can be triggered on the video signal (e.g., one of the video timing pulses).

A variable radius on the circle pattern produced by generator 175 effectively allows the pattern to be adjusted to correspond with the expanded laser beam spot. In alternative embodiments, the circle pattern can be fixed on the monitor screen, and the laser spot size can be adjusted with a lens on the laser output, or by moving back and forth from the target to change the spot size.

Figure 1E:
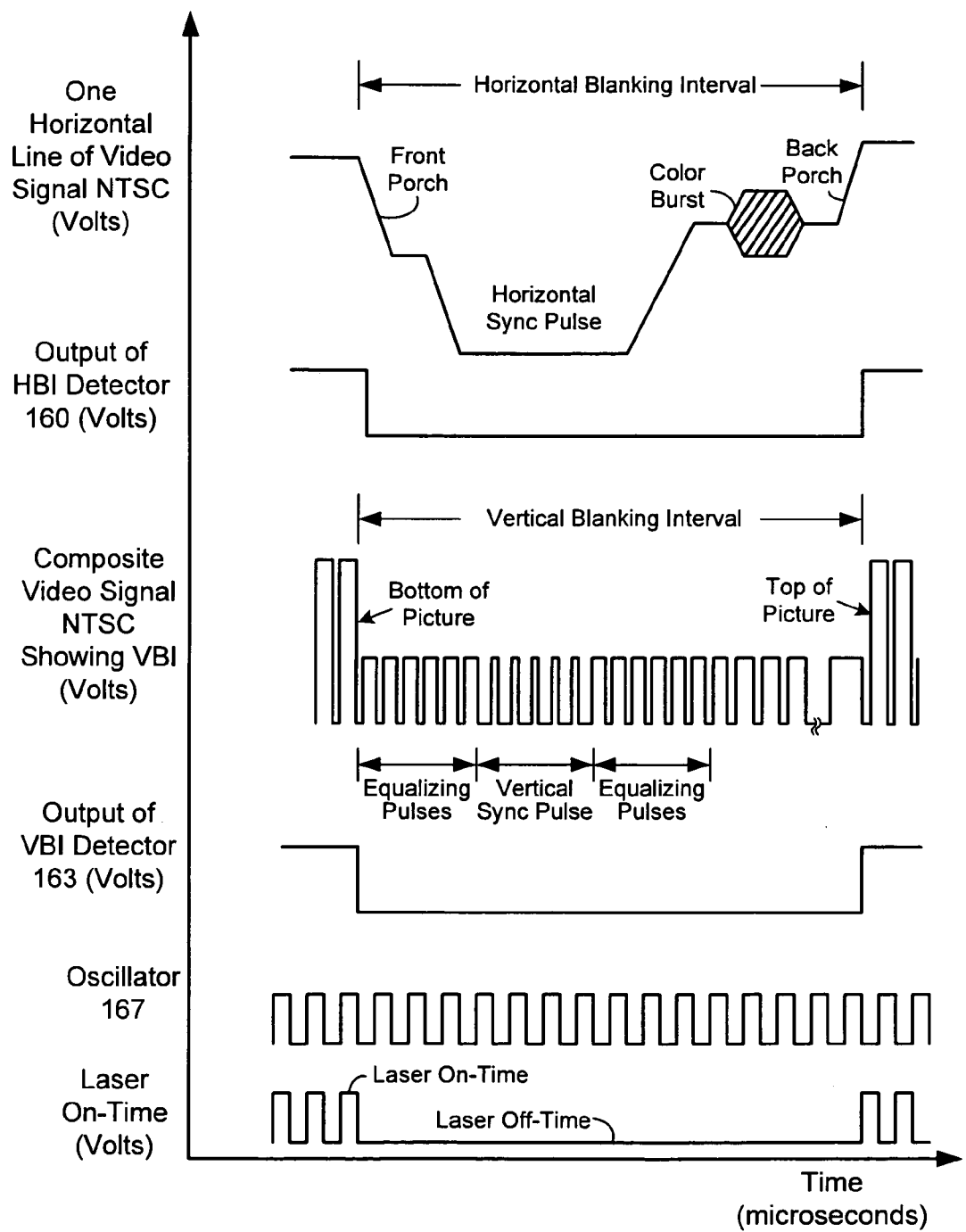
FIG. 1e shows timing diagrams that illustrate a power density reduction technique where the laser of the system shown in FIG. 1a is turned off during certain times and video housekeeping operations, in accordance with an embodiment of the present invention.

As can be seen from FIG. 1d and the timing diagram of FIG. 1e, the output of gate 169 of the conditioning electronics 121 is high only when the following conditions are met: the output of the oscillator 167 is high; the output of the HBI detector 160 is high (meaning that the HBI is not occurring); the output of the VBI detector 163 is high (meaning that the VBI is not occurring); and the output of the image detector 165 is high (meaning that a scan line of the camera 105 is currently active). The driver 171 of electronics 121 can then be used to drive the signal output by gate 169 to the modulation input of the laser 101. As can further be seen in FIG. 1e, the laser on time is significantly reduced by using the conditioning electronics, thereby also reducing the power density of laser 101.

As is known, there are a number of laser classes. For instance, ANSI Z136.1-2007 is one standard that provides for definition of various laser classes. In some example embodiments, it may be desirable to operate the system as a Class 3 laser system (which may involve a power density, for example, in the range of less than 500 mW). One benefit of the power density reduction techniques described herein, is that they allow for using a laser that is effectively rated above the limit for the desired class, because the power density reduction enabled by power density reduction techniques #1, #2, and/or #3 lowers the power density to bring it within the desired class (e.g., Class 3 or other target power density regime).

Variations on the techniques will be apparent in light of this disclosure. For instance, in the case of LCD displays, the timing may be different in the Digital Visual Interface (DVI) than described above for the NTSC RS-170 standard. Similarly, different camera display formats may require specific types of signal conditioning. Although this discussion herein is provided in the context of the NTSC RS-170 (analog) video format, similar techniques can be implemented using other analog formats as well as digital television formats. Thus, the concepts as described herein can be readily applied in the context of numerous applications and standards.

Handheld System

FIGS. 2a, 2b, and 2c demonstrate a handheld gas leak detector 200 that includes the detection system shown in FIG. 1a, configured in accordance with an embodiment of the present invention. As can be seen, the detector 200 is shaped like a gun having a handle 203 and barrel 205, so as to allow a user to point the aperture 201 at a target area to search for leaks. The detector 200 can be powered on and off by switch 211, which effectively can be used to mechanically switch the battery 125 in and out of circuit, such that when switch 211 is on, detector 200 can be trigger operated, and when switch 211 is off, detector 200 can be stored or otherwise dormant. A number of operational schemes can be used here.

For instance, in one such example embodiment, when trigger 207 is pressed, an enable signal is provided directly to the laser 101 and camera 105 (and to any other supporting circuitry that needs to be enabled), so that leaks can be detected as described herein. In other cases, depressing the trigger 207 can be used to activate the optional processor 123, which then in turn enables the various components of the detection system to operate for leak detection purposes.

In any such cases, when the trigger 207 is pressed, a laser beam from laser 101 passes through the aperture 201 to the target area within the FOV 105a of camera 105. Should the target gas be present, that gas will absorb radiation of the laser beam, thereby allowing the thermal camera 105 to image the gas leak. The gas leak will then appear on the camera monitor 105b. Should wavelength hopping mitigation techniques #1 or #2 be employed, indicator 119 is also provided, such as a green LED that lights (e.g., or an audible alarm that sounds off) when the laser is on-resonance with the target gas, thereby giving the user a visual cue when on-resonance detection is occurring.

As can be seen in FIG. 2c, the various components of the detection system can be integrated into the handheld gun-like housing. In this example embodiment, wavelength hopping mitigation technique #2 is not employed. Any number of suitable component layouts can be used, depending on factors such as included functionality and number of options employed as well as the housing form factor and amount of available space therein.

Figure 3A:
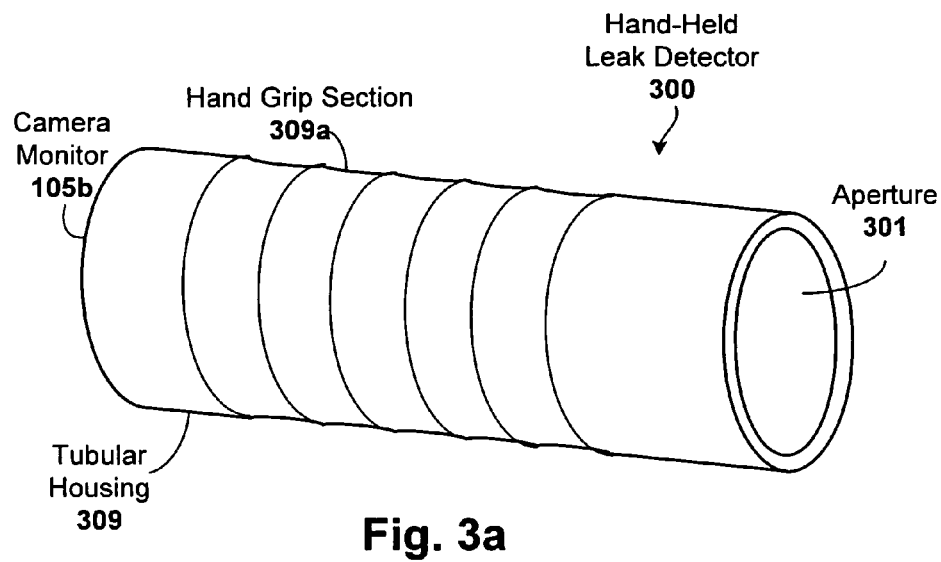
FIG. 3a is perspective view of a handheld gas leak detector, configured in accordance with another embodiment of the present invention.
Figure 3B:
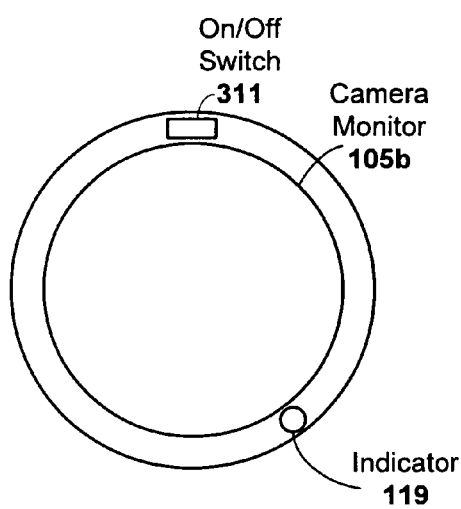
Figure 3C:
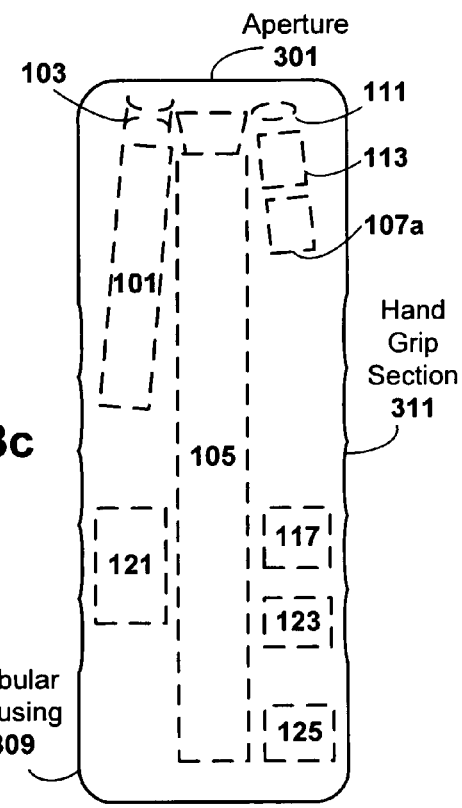
FIG. 3c is top-view of the handheld gas leak detector shown in FIG. 3a, with internal components shown in dashed lines.

FIGS. 3a, 3b, and 3c demonstrate a handheld gas leak detector 300 that includes the detection system shown in FIG. 1a, configured in accordance with another embodiment of the present invention. As can be seen, the detector 300 has the form factor of a telescope and includes tubular housing 309 having a hand grip section 309a, and is configured to allow a user to point the aperture 301 at a target area to search for leaks. In alternative embodiments, housing 309 could be more square or rectangular in nature (as opposed to tubular). Other housing shapes amenable to handheld operation will be apparent in light of this disclosure. The detector 300 can be powered on and off by switch 311, which effectively can be used to mechanically switch the battery 125 in and out of circuit, such that when switch 311 is on, detector 300 is operational, and when switch 311 is off, detector 300 can be stored or otherwise dormant. A number of operational schemes can be used here.

For instance, in one such example embodiment, when switch 311 is pressed or otherwise turned on, an enable signal is provided directly to the laser 101 and camera 105 (and to any other supporting circuitry that needs to be enabled), so that leaks can be detected as described herein. In other cases, depressing the switch 311 can be used to activate the optional processor 123, which then in turn enables the various components of the detection system to operate for leak detection purposes. Note that the position of switch 311 can be moved to the side of the tube 309 (e.g., within the grip section 311) for convenient access by user.

In any such cases, when the switch 311 is activated, a laser beam from laser 101 passes through the aperture 301 to the target area within the FOV 105a of camera 105. Should the target gas be present, that gas will absorb radiation of the laser beam, thereby allowing the thermal camera 105 to image the gas leak. The gas leak will then appear on the camera monitor 105b. Should wavelength hopping mitigation techniques #1 or #2 be employed, indicator 119 is also provided, such as a green LED that lights when the laser is on-resonance with the target gas, as previously explained (other on-resonance indicators, such as audible alarm or a vibration may be used also, as previously explained).

As can be seen in FIG. 3c, the various components of the detection system can be integrated into the handheld tubular housing 309. In this example embodiment, wavelength hopping mitigation technique #2 is not employed. As will be apparent in light of this disclosure, other embodiments may employ wavelength hopping mitigation technique #2 instead of mitigation technique #1, or no such techniques. Any number of suitable component layouts can be used, depending on factors such as included functionality and number of options employed as well as the housing form factor and amount of available space therein.

FIG. 4 illustrates an image of the infrared absorption of a gas detected by the system shown in FIG. 1a, in accordance with an example embodiment of the present invention. As can be seen, monitor 105b is rectangular in this example embodiment, but other embodiments may have different shaped monitors. As can further be seen, the laser beam is round, such that the image of the reflected laser beam shown on the monitor 105b is round also. Other embodiments may have different shaped laser beams (square, etc) and/or monitors (such as the round monitor 105b shown in FIG. 3b). The image of the gas absorption shadow can also be seen, thereby allowing a user to visually detect gas leaks. There may also be a portion of unused monitor area, as further shown.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A gas leak imaging system, comprising:
    an unstabilized $CO_2$ infrared laser for providing a laser beam having at least one wavelength that is absorbable by a target gas comprising sulfur hexafluoride ($SF_6$);
    a thermal imaging camera having a field of view and for imaging absorption of the at least one wavelength by the target gas; and a diverging lens for expanding the laser beam toward the field of view; wherein the system is contained in a handheld housing further comprising
    (a) circuitry for mitigating the effects of wavelength hopping comprising a detector for receiving light from the unstabilized laser and generating an electrical signal representative of intensity associated with that light and a circuit for receiving the electrical signal, indicating when the at least one wavelength that is on-resonance with absorption lines of the target gas; or
    (b) a spoiler in said unstabilized laser to stop laser wavelengths that are not on-resonance with the absorption lines of the target gas;
    and wherein said gas leak imaging system further includes circuitry for power reduction.

2. The system of claim 1 wherein the camera is a longwave infrared camera.

3. The system of claim 1 wherein the circuit for indicating when the at least one wavelength that is on-resonance with absorption lines of the target gas comprises:
    a comparator for receiving the electrical signal and comparing that signal to a known threshold that is representative of a minimum required light intensity signal; and
    an indicator for indicating, based on the output of the comparator, when the at least one wavelength is on-resonance with absorption lines of the target gas.

4. The system of claim 1 wherein the light received by the detector is one of reflected back from the field of view, or split off form the laser beam provided by the unstabilized laser.

5. The system of claim 1 wherein the circuitry for reducing power density comprises an osicallator for modulating the unstabilized laser.

6. The system of claim 1 wherein the circuitry for reducing power density comprises: a horizontal blanking interval detector for receiving a video output of the thermal imaging camera, and detecting when the horizontal blanking interval is occurring, thereby allowing the unstabilized laser to be turned off during that interval.

7. The system of claim 1 wherein the circuitry for reducing power density comprises: an image detector for receiving a video output of the thermal imaging camera, and detecting when a scan line of the camera is active, thereby allowing the unstabilized laser to be turned off when no image data is present.

8. The system of claim 1 wherein the circuitry for reducing power density comprises at least one of: an oscillator for providing a laser modulating frequency; a vertical blanking interval detector for receiving a video output of the thermal imaging camera, and detecting when the vertical blanking interval is occurring, thereby allowing the unstabilized laser to be turned off during that interval; a horizontal blanking interval detector for receiving a video output of the thermal imaging camera, and detecting when the horizontal blanking interval is occurring, thereby allowing the unstabilized laser to be turned off during that interval; and an image detector for receiving a video output of the thermal imaging camera, and detecting when a scan line of the camera is active, thereby allowing the unstabilized laser to be turned off when no image data is present.

9. A gas leak imaging method, comprising: providing a laser beam from an unstabilized $CO_2$ infrared laser to a field of view, the laser beam having at least one wavelength that is absorbable by a target gas comprising sulfur hexafluoride ($SF_6$); expanding the laser beam toward the field of view; and imaging absorption of the at least one wavelength by the target gas; wherein the unstabilized laser is contained in a handheld device that is capable of carrying out the method and comprises (a) circuitry for mitigating the effects of wavelength hopping comprising a detector for receiving light from the unstabilized laser and generating an electrical signal representative of intensity associated with that light and a circuit for receiving the electrical signal, indicating when the at least one wavelength that is on-resonance with absorption lines of the target gas; or (b) a spoiler in said unstabilized laser to stop laser wavelengths that are not on-resonance with the absorption lines of the target gas;

and wherein said gas leak imaging system further includes circuitry for power reduction.

* * * * *